United States Patent [19]

Sakai

[11] Patent Number: 4,959,322
[45] Date of Patent: Sep. 25, 1990

[54] CULTURING APPARATUS

[75] Inventor: Mari Sakai, Tokyo, Japan

[73] Assignee: W. L. Gore & Associates, Inc., Newark, Del.

[21] Appl. No.: 320,147

[22] Filed: Mar. 7, 1989

[51] Int. Cl.$^5$ .............................................. C12M 1/12
[52] U.S. Cl. .................................... 435/311; 435/286
[58] Field of Search ............... 435/286, 310, 311, 313, 435/284; 210/150, 151

[56] References Cited

U.S. PATENT DOCUMENTS

| 4,564,373 | 1/1986 | Schnitz et al. | 210/638 |
| 4,725,548 | 2/1988 | Karrer | 435/311 |

FOREIGN PATENT DOCUMENTS

| 0112155 | 6/1984 | European Pat. Off. | |
| 155237 | 9/1985 | European Pat. Off. | 435/286 |
| 59-175877 | 10/1984 | Japan . | |
| 60-234580 | 11/1985 | Japan . | |
| 61-100190 | 5/1987 | Japan . | |
| 87/03615 | 12/1985 | PCT Int'l Appl. | |
| 2059436 | 4/1981 | United Kingdom . | |
| 2075547 | 11/1981 | United Kingdom . | |

OTHER PUBLICATIONS

Bunri Gijutsu, Separation Technology, vol. 14, No. 4, (1984).

Primary Examiner—James C. Yeung
Attorney, Agent, or Firm—Gary A. Samuels

[57] ABSTRACT

The present invention concerns a culturing apparatus, the object of said invention being to provide an apparatus which allows an efficient oxygen supply to be achieved without damaging the cells, microorganisms or tissues that are to be cultured.

1 Claim, 3 Drawing Sheets

CULTURING APPARATUS

FIELD OF INVENTION

The present invention concerns the culturing of cells, microorganisms and tissues, as well as bioreactors utilizing oxygen in such culturing, and especially concerns the culturing of aerobic bacteria and easily damaged animal cells, etc.

BACKGROUND OF THE INVENTION

Means used to supply oxygen in culturing apparatus and bioreactors used for the culturing of cells, microorganisms and tissues include absorption from the surface of the culture solution, blowing in by means of a sparger, and aeration by means of agitation, etc. Furthermore, methods in which oxygen is supplied via a membrane have been described in Japanese Laid-Open Patent Application (Koaki) No. 57-159535, Japanese Laid-Open Patent Application (Kokai) No. 59-175877, Japanese Laid-Open Patent Application (Kokai) No. 60234580 and Japanese Laid-Open Patent Application (Kokai) No. 61-100190, etc.

Furthermore, in *Bunri Gijutsu*, Separation Technology, Vol. 14, No. 4 (1984), a method is introduced in which the efficiency of acetic acid fermentation is increased by fixing acetic acid bacteria (which are aerobic bacteria) to the outside of a hydrophobic hollow membrane structure, and causing air to flow through said hollow membrane structure.

In the abovementioned conventional systems involving absorption from the surface of the culture solution, there are limits to the oxygen supply capacity, and this capacity is unavoidably insufficient in cases where the culture tank is large in size. In the case of blowing in by means of a sparger of aeration by agitation, there is a high possibility of bubble or agitation damage in the case of delicate cells such as animal cells, etc., or cells which have little resistance to a shearing force.

The methods described in the aforementioned laid-open patent applications and *Bunri Gijutsu*, Separation Technology, which solve the abovementioned problems, supply $O_2$ to a culture solution located on the outside of a semi-permeable membrane tube without generating any bubbles; this is accomplished by causing $O_2$ to flow through the interior of said semi-permeable membrane tube. However, since this is a calm supply state which lacks the agitating action that accompanies the rise of bubbles generated in the culture solution, a bias tends to be generated in the concentration of solute oxygen in the culture solution inside the tank, so that the concentration of solute oxygen in the culture solution near the circumference of the semi-permeable membrane is constantly high in relative terms; accordingly, the supply efficiency is still insufficient, so that it is difficult to obtain desirable results using such a method, especially in the case of a large apparatus.

SUMMARY OF THE INVENTION

1. A culturing apparatus in which a gas is caused to contact a culture solution via a gas-permeable membrane so that said gas is supplied to said culture solution, comprising:
   (a) a culture solution flow region which is virtually surrounded by the aforementioned gas-permeable membrane,
   (b) a culture solution supply means which supplies culture solution to the aforementioned culture solution flow region from a supply source, and
   (c) a gas supply region facing the aforementioned gas-permeable membrane which supplies gas to the flowing culture solution.

2. A culturing apparatus in which a gas is caused to contact a culture solution via a gas-permeable membrane so that said gas is supplied to said culture solution, comprising:
   (a) a culture solution flow region which is virtually surrounded by the aforementioned gas-permeable membrane,
   (b) a culture solution supply means which supplies culture solution to the aforementioned culture solution flow region from a supply source, and
   (c) a degassing region which degasses the flowing culture solution and a gas supply region which supplies gas to the flowing culture solution, both facing the aforementioned gas-permeable membrane.

DETAILED DESCRIPTION OF THE INVENTION WITH REFERENCE TO THE DRAWINGS

A culture solution is supplied by a supply means such as a pump, etc., from a supply source such as a culture tank, etc., to a culture solution flow region which is virtually surrounded by a gas-permeable membrane. Specifically, this culture solution flows through the aforementioned culture solution flow region, so that the culture solution in contact with the aforementioned gas-permeable membrane is constantly renewed and effectively supplied with a gas such as oxygen, etc.

Such a supplying of gas via a gas-permeable membrane is an efficient method of supply which does not require the generation of bubbles, etc. Since no bubbles are generated in the culture tank or in the vicinity of the gaspermeable membrane, damage to delicate microorganisms or cells, etc., can be avoided.

Since the aforementioned culture solution is fed into a flow region inside a gas-permeable membrane by a supply means from a supply source such as a culture tank, and is then returned to said supply source from said flow region, flow of the culture solution is also effected inside the aforementioned supply source, so that the amount of solute oxygen in the culture solution is made uniform.

Figure 1:
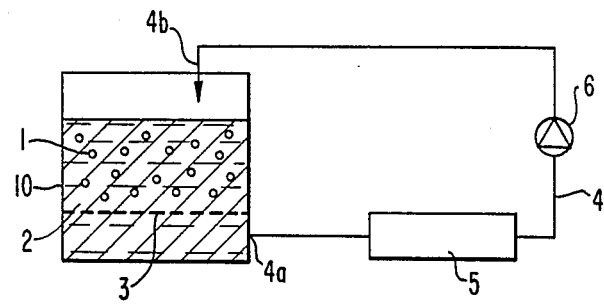
FIGS. 1 and 2 illustrate examples of the overall construction of the apparatus of the present invention.

FIG. 1 shows one example of the overall construction of the apparatus. The interior of a culture tank (10) is partitioned by a mesh filter (3) which does not allow the passage of the bodies being cultured (1) (e.g., cells, microorganisms or tissues, etc.). The aforementioned bodies being cultured (1), or a support on which said cultured bodies (1) are fixed, are positioned on one side of the abovementioned partition, and a culture solution (2) is accommodated in this space. The intake port (4a) of a culture solution circulation line (4) opens into the space on the other side of the abovementioned partition. A gas-permeable membrane module (5) is installed in the aforementioned culture solution circulation line (4), and the discharge port (4b) of said line (4) opens into the space on the aforementioned first side of the abovementioned partition. The aforementioned culture solution (2) is supplied and circulated by a supply means (6) such as a pump.

Figure 2:
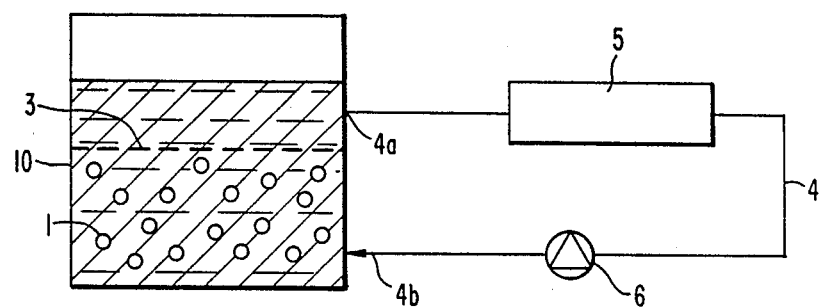

The culture tank (10) which constitutes the culture solution supply source should naturally be maintained at a temperature which is suitable for the culturing operation in question; meanwhile, it is desirable that the temperature conditions in the gas-permeable membrane module (5) be suitable for gas supply. Accordingly, the culture solution conducted into said module (5) may be appropriately heated or cooled. In cases where the solution temperature in the culture tank (10) and the solution temperature of the solution returned to the culture tank via the discharge port (4b) are the same, or where the solution temperature at the discharge port is lower, the arrangement shown in FIG. 1 is suitable. However, in cases where the solution temperature at the discharge port (4b) is conversely higher than the solution temperature inside the culture tank (10), it is desirable to install the intake port (4a) in the upper part of the culture tank (10) and the discharge port (4b) in the lower part of said tank (10) as shown in FIG. 2, so that a relationship which is the opposite of that shown in FIG. 1 is established. Specifically, as a result of either of these respective arrangements, a relationship which causes the culture solution discharged from the discharge port (4b) to flow toward the intake port (4a) is effectively established inside the culture tank (10). As a result, the concentration of solute gas (oxygen) in the culture solution (2) inside the tank (10) is constantly kept uniform.

Figure 3:
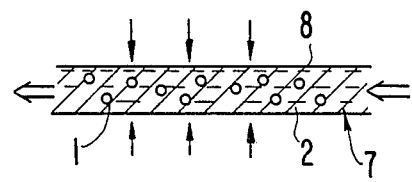
FIGS. 3 and 4 illustrate modifications of the gas-permeable membrane tube in the gas diffusion module of the aforementioned apparatus.
Figure 4:
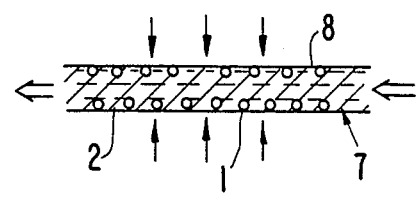

The gas-permeable membrane (8) in the aforementioned gas-permeable membrane module (5) allows gas to pass through without allowing the culture solution to pass through. A culture solution flow region (7) is formed by said gas-permeable membrane (8). In the case of the arrangements illustrated in FIGS. 1 and 2, only the culture solution passes through said flow region (7), and gas is supplied and diffused into said solution from the outside via the gas-permeable membrane (8). In regard to this flow region (7), however, it would also be possible to remove the aforementioned filter (3) so that both the bodies being cultured (1) and the culture solution (2) pass together through the flow region (7), as shown in FIG. 3. Alternatively, it would also be possible to fix the bodies being cultured (1) in place inside the flow region (7) formed by the aforementioned gas-permeable membrane (8), and to allow only the culture solution to pass through, as shown in FIG. 4. Methods which can be used for such fixing include universally known methods such as ionic bonding, covalent bonding and inclusion methods, etc. Such fixing can easily be accomplished by such methods.

Figure 5:
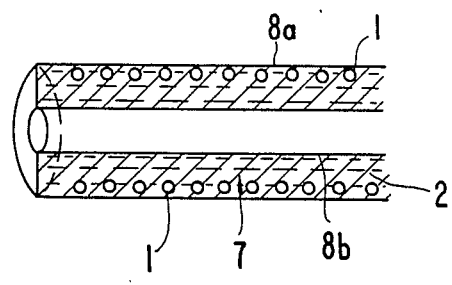
FIG. 5 illustrates a double tube which constitutes another example of the aforementioned membrane tube.

FIG. 5 illustrates yet another arrangement of the aforementioned flow region (7). In this arrangement, specifically, a double tube made of the aforementioned gas-permeable membrane is used, and this double tube is arranged so that a gas such as $O_2$, etc., is supplied, while $CO_2$ and/or other product gasses are at the same time removed. A flow region (7) for the culture solution (2) is formed between the outside tube (8a) and the inside tube (8b). Oxygen, etc., passes through the outside tube (8a) and is thus supplied to the culture solution (2), while product gasses from the bodies being cultured (1), such as $CO_2$ gas, etc., are expelled via the inside tube (8b).

Figure 6:
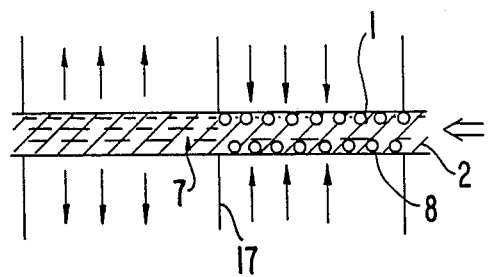
FIGS. 6 and 7 illustrate other working configurations of the structure inside the gas-permeable membrane module.

Furthermore, such supply and removal of respective gases may also be accomplished as shown in FIG. 6. The space outside the gas-permeable membrane (8) can be divided by a partition (17), with the pressure on one side of the partition lowered so that product gasses are removed, and the pressure on the other side of the partition appropriately raised so that gas is supplied.

Figure 7:
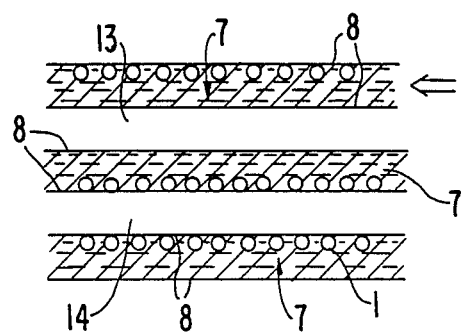

Furthermore, it would also be possible to perform both the removal of product gases from the culture solution and the supply of a gas such as fresh $O_2$, as indicated in FIG. 7. Flat gas-permeable membranes (8) are installed in a multi-layer configuration, forming culture solution flow regions (7) in alternate spaces between said membranes, and forming reduced-pressure regions (13) and pressurized regions (14) between the resulting culture solution flow regions (7, 7).

Furthermore, in addition to the abovementioned tube-form or flat gas-permeable membranes, the apparatus of the present invention could also employ a spiral-form or pleated module.

In the supply of gas to the culture solution via the abovementioned gas-permeable membrane (8), the fact that said gas-permeable membrane (8) is generally an extremely thin membrane makes it difficult from a practical standpoint to supply gas using an extremely large pressure differential. Furthermore, since this supply is normally accomplished efficiently, there is generally no need to employ an especially large pressure differential. However, in cases where there is a need for a large pressure differential, it is desirable that the supply operation be performed at a pressure differential of 0.15 $kg/cm^2$ or less in order to avoid damage to the bodies being cultured (1) as a result of the generation of gas bubbles in the culture solution.

The use of a water-repellent porous membrane as the aforementioned gas-permeable membrane (8) is desirable in that the properties of such a material can be utilized in order to block the passage of the culture solution, and in that the desired effective contact with the gas can be obtained using a membrane in which relatively large pores are formed. A membrane made of a fluoro- resin or silicone resin (which presents no particular danger of elution) may be employed, or a gas-separating membrane such as an oxygen enrichment membrane may be used. One example of a desirable gas-permeable membrane is a tube or membrane material with a porosity of 75 to 95 vol percent and a maximum pore size of approximately 0.02 to 3 microns, which is formed by drawing a polytetrafluoroethylene film so that said film is made porous according to U.S. Pat. No. 3,953,566. The gas permeability of this membrane is approximately 3 to 4.8 ml/min.cm2.

As was described above, the present invention makes it possible to supply a gas to a culture solution continuously by means of an in-line system. This apparatus is able to cope effectively even with large equipment, and allows an efficient supply of oxygen, etc., to be obtained. Accordingly, the present invention has great industrial merit.

I claim:

1. A culturing apparatus in which a gas is caused to contact a culture solution via a gas-permeable membrane so that said gas is supplied to said culture solution, comprising:
(a) gas-permeable membrane module which surrounds a gas-permeable membrane tube which allows gas to pass through without allowing culture solution to pass through, and the aforementioned gas-permeable membrane module is divided by a partition, with the pressure on one side of the partition lowered so that product gasses are removed from the culture solution, and the pressure on the other side of the partition is raised so that gas is supplied to the culture solution and
(b) a culture solution supply means, which supplies culture solution to the aforementioned gas-permeable membrane from a supply source.

* * * * *